United States Patent [19]

Harfenist

[11] Patent Number: 4,616,032

[45] Date of Patent: Oct. 7, 1986

[54] USE OF NITROGEN HETEROCYCLIC COMPOUNDS

[75] Inventor: Morton Harfenist, Chapel Hill, N.C.

[73] Assignee: Burroughs Wellcome Co., Research Triangle Park, N.C.

[21] Appl. No.: 688,704

[22] Filed: Jan. 4, 1985

[30] Foreign Application Priority Data

May 1, 1984 [GB] United Kingdom ............... 8400202

[51] Int. Cl.$^4$ ........................................ A61K 31/385
[52] U.S. Cl. ................................................. 514/436
[58] Field of Search ......................................... 514/436

[56] References Cited

U.S. PATENT DOCUMENTS 3,905,989  9/1975  Hodson et al. .................. 260/308 D
4,091,108  5/1978  Batchelor et al. ................. 514/436

OTHER PUBLICATIONS

Sheehan, J. Clin. Psychiatry, 45:7 (1984), pp. 29-36.

Primary Examiner—Stanley J. Friedman
Attorney, Agent, or Firm—Donald Brown

[57] ABSTRACT

A method of inhibiting monoamine oxidase-A in a mammal such as man, comprising administration to said mammal of an effective amount of a compound of formula (I') or a physiologically acceptable salt, or a prodrug or metabolite thereof.

In formula (I')

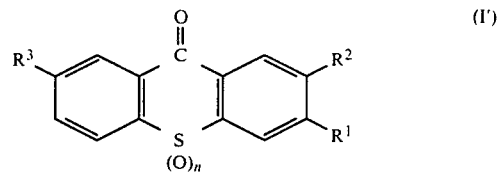

n is 0, 1 or 2;

one of $R^1$ and $R^2$ is hydrogen and the other is a tetrazol-5-yl group optionally substituted by one or more $C_{1-4}$ alkyl groups; and $R^3$ is selected from hydrogen, saturated and unsaturated aliphatic hydrocarbon moieties containing from 1 to 4 carbon atoms, groups $OR^4$ (where $R^4$ is selected from hydrogen and saturated and unsaturated aliphatic hydrocarbon moieties containing from 1 to 4 carbon atoms), halo, groups of formula —$NR^5R^6$ (where $R^5$ and $R^6$ are independently selected from hydrogen $C_{1-4}$ alkyl and hydroxy $C_{1-4}$ alkyl, provided that the total number of carbona atoms in $R^5$ and $R^6$ does not exceed 4), amino $C_{1-4}$ alkylamino and morpholino.

The compounds of formula (I') and their physiologically acceptable salts are thus used in methods of prophylaxis and treatment of mental disorders such as depression.

4 Claims, No Drawings

USE OF NITROGEN HETEROCYCLIC COMPOUNDS

The present invention relates to tricyclic compounds having valuable monoamine oxidase inhibitory activity.

Monoamine oxidase (MAO) is a brain enzyme believed to be responsible for intraneuronal catalysis of oxidation of biogenic amine neurotransmitters to inactive forms. It is understood to occur as two independent enzymes normally designated MAO-A and MAO-B (White and Glassman, J. Neurochem., 29, 989–997, (1977) and Tipton et al, "Monoamine Oxidase and its Selective inhibitors", Beckmann and Riederer, Eds., Mod. Probl. Pharmacopsychiat., 19 15–30, Karger, Basel (1983)). MAO inhibition has been found to elevate neurotransmitter concentration in the brain. MAO inhibition has been found to elevate neurotransmitter concentration in the brain. MAO inhibitors are used therapeutically in the treatment of a wide variety of conditions, especially depression, particularly when characterized by anxiety obessional neuroses, or appetite disorders.

We have now discovered that certain new thioxanthen-9-one derivatives of formula (I) as defined hereinbelow, posseses advantageous MAO-A inhibitory properties which render the compounds useful for the treatment of mental disorders.

In formula (I)

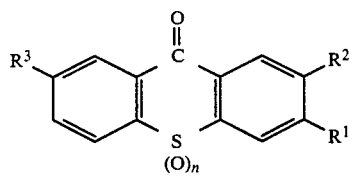

wherein
n is 0, 1 or 2;
one of $R^1$ and $R^2$ is hydrogen and the other is a tetrazol-5-yl group optionally substituted by one or more $C_{1-4}$ alkyl groups; and
$R^3$ is selected from hydrogen, saturated and unsaturated aliphatic hydrocarbon moieties containing from 1 to 4 carbon atoms, groups $OR^4$ (where $R^4$ is selected from hydrogen and saturated and unsaturated aliphatic hydrocarbon moieties containing from 1 to 4 carbon atoms), halo, groups of formula —$NR^5R^6$ (where $R^5$ and $R^6$ are independently selected from hydrogen, $C_{1-4}$ alkyl and hydroxy $C_{1-4}$ alkyl, provided that the total number of carbon atoms in $R^5$ and $R^6$ does not exceed 4), amino-$C_{1-4}$ alkylamino and morpholino;
provided that:
when $R^1$ is unsubstituted tetrazol-5-yl, $R^2$ is hydrogen and $R^3$ is selected from hydrogen, chlorine, methyl, ethyl and t-butyl, then n is 1; and
when $R^1$ is 2-methyltetrazol-5-yl and $R^2$ and $R^3$ are both hydrogen, then n is 0 or 1; and physiologically acceptable salts thereof.

Certain thioxanthen-9-ones, and their 10-oxides and 10,10-dioxides, said to be anti-allergic agents, are described respectively in UK patent specification No. 1,458,185 and U.S. Pat. Nos. 4,091,108 and 3,905,989 (hereinafter referred to as the 'Batchelor and Hodson Specifications'). We have now discovered that as well as the compounds of formula (I), some compounds disclosed in the latter specifications are also MAO-A inhibitors and are useful in the therapy of mental disorders such as those discussed above. The aforementioned known compounds and the compounds of formula (I), together constitute a class of compounds of formula (I') and their physiologically acceptable salts.

In formula (I')

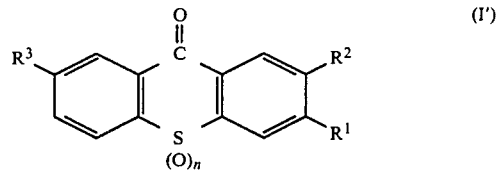

n is 0, 1 or 2;
one of $R^1$ and $R^2$ is hydrogen and the other is a tetrazol-5-yl group optionally substituted by one or more $C_{1-4}$ alkyl groups; and
$R^3$ is selected from hydrogen, saturated and unsaturated aliphatic hydrocarbon moieties containing from 1 to 4 carbon atoms, groups $OR^4$ (where $R^4$ is selected from hydrogen and saturated and unsaturated aliphatic hydrocarbon moieties containing from 1 to 4 carbon atoms), halo, groups of formula —$NR^5R^6$ (where $R^5$ and $R^6$ are independently selected from hydrogen, $C_{1-4}$ alkyl and hydroxy $C_{1-4}$ alkyl, provided that the total number of carbon atoms in $R^5$ and $R^6$ does not exceed 4), amino-$C_{1-4}$ alkylamino and morpholino.

Included within the scope of the compounds of formula (I') are the physiologically acceptable salts of such compounds. In particular, the latter salts and also the physiologically acceptable salts of compounds of formula (I) may be the acid addition salts of compounds wherein $R^3$ represents a group of formula —$NR^5R^6$, and amino $C_{1-4}$ alklamino group or a morpholino group, for example those derived from hydrochloric, hydrobromic, phosphoric, malic, maleic, fumaric, citric, sulphuric, lactic and tartaric acids.

In formulae (I) and (I') when $R^3$ and/or $R^4$ is a saturated or unsaturated $C_{1-4}$ aliphatic hydrocarbon moiety, these groups may be selected independently from, for example $C_{1-4}$ alkyl, $C_{2-4}$ alkenyl and $C_{2-4}$ alkynyl groups.

A particular class of the compounds of formula (I) and their physiologically acceptable salts, are those wherein $R^3$ is selected from hydrogen, saturated and unsaturated aliphatic hydrocarbon moieties containing from 1 to 4 carbon atoms, groups $OR^4$ (where $R^4$ is selected from hydrogen and saturated and unsaturated aliphatic hydrocarbon moieties containing from 1 to 4 carbon atoms), halo, groups of formula —$NR^5R^6$ (where $R^5$ and $R^6$ are independently selected from $C_{1-4}$ alkyl and hydroxy-$C_{1-4}$ alkyl, provided that the total number of carbon atoms in $R^5$ and $R^6$ does not exceed 4), amino-$C_{1-4}$ alkylamino and morpholino.

Particularly preferred compounds of formula (I) and where appropriate, of formula (I') include the following compounds and their physiologically acceptable salts;

A. 7-isopropyl-3-(2-methyl)-2H-tetrazol-5-yl)thioxanthen-9-one 10,10-dioxide.

B. 3-(2-methyl-1H-tetrazol-5-yl)thioxanthen-9-one 10,10-dioxide.

C. 3-(1-methyl-1H-tetrazol-5yl)thioxanthen-9-one 10,10-dioxide.

Thus, the present invention includes a method of inhibiting monoamine oxidase-A(MAO-A) in mammals such as humans. This method comprises administration to a mammal which has been identified as being in need such inhibition a compound of formula (I') as hereinbefore defined or a physiologically acceptable salt thereof in an amount sufficient to inhibit the monoamine oxidase-A. The invention also provides a method of prophylaxis or treatment of a mental disorder in mammals especially humans. This method comprises administration to a mammal which has been identified as having a mental disorder therapeutically effective amount of a compound of formula (I') as hereinbefore defined or a physiologically acceptable salt thereof.

In such a method the mental disorder may for example be:

(a) depression, particularly that characterised by anxiety or obsessional neuroses, or an atypical depression, e.g. accompanied by a personality disorder;

(b) obsessive compulsive states;

(c) anxiety states, e.g., which are accompanied in an acute phase by panic attacks; and (d) certain appetite disorders, e.g. bulimia and anorexia.

The compounds of formula (I') and their physiologically acceptable salts may be administered by for example the oral, rectal or parenteral route. In general, the compound, may be administered at a dosage in the range of 1 mg to 100 mg per kg of recipient bodyweight per day, although the precise dosage will naturally depend on a number of clinical factors, for example, the type (i.e. human or other mammal), age of the recipient, the condition under treatment and its severity. For administration of the compounds by the oral route a dosage regime of 1 to 50 mg per kg per day preferably 10 to 40, e.g. about 25 mg per kg per day may be used. For administration by the parenteral route a dosage regime of 0.2 to 10 mg per kg per day, advantageously 1 to 5 mg per kg per day, e.g., about 2 mg per kg per day is generally preferred.

While it is possible to administer the compounds of formula (I) as the raw compound, it is highly desirable to administer it in the form of a pharmaceutical formulation. The present invention thus further provides pharmaceutically acceptable formulations comprising as active ingredient, one or more compounds of formula (I') (as defined above) or physiologically acceptable salt(s) thereof in association with at least one pharmaceutical carrier or excipient. The pharmaceutical formulations may be adapted for oral, parenteral or rectal administration.

The formulations may conveniently be presented in unit dosage form and may be prepared by any of the methods well known in the art of pharmacy. Such methods include the step of bringing into association the active ingredient with the carrier which may comprise one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid or as an oil-in-water liquid emulsion or a water-in-oil liquid emulsion.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for rectal administration may be presented as a suppository with the usual carriers such as cocoa butter.

Formulations suitable for parenteral administration include aqueous sterile injection solutions which may contain antioxidants, buffers, bacteriostats and solutes which render the formulation isotonic with the blood of the intended recipient; and aqueous and nonaqueous sterile suspensions which may include suspending agents and thickening agents. The formulations may be presented in unitdose or multidose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powder, granules and tablets of the kind previously described.

Preferred unit dosage formulations are those containing a daily dose or unit daily subdose, as hereinabove recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavouring agents.

Thus according to a further feature of the present invention we provide a process for the preparation of compounds of formula (I') (as hereinbefore defined) and their physiologically acceptable salts, the said process comprising:

(a) reacting a compound of formula (II)

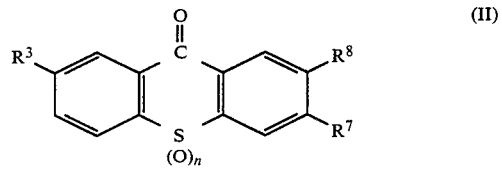

(wherein $R^3$ and n are as previously defined, and one of $R^7$ and $R^8$ is hydrogen and the other is a precursor to an optionally alkylated tetrazol-5-yl group) with hydrazoic acid; or (b) oxidising a compound of formula (III)

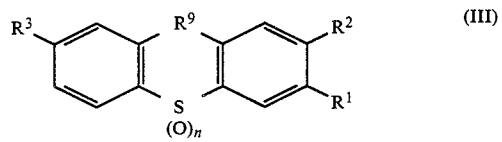

(wherein $R^1$–$R^3$ and n are as defined above).

Where appropriate, in either of processes (a) and (b) above, the reactant compound of formula (II) or (III) may be provided in the form of a suitable salt thereof. The above processes, where appropriate, may also include one or more of the following optional steps:

(i) Converting the resultant compound of formula (I') or salt thereof, or a precursor therefor, into a physiologically acceptable salt thereof.

(ii) Where the group $R^3$ in the resultant compound of formula (I') is a displaceable group, for example a halogen such as fluorine, converting the compound to another compound of formula (I') wherein $R^3$ is a group $OR^4$ or $-NR^5R^6$ as defined, or an amino-$C_{1-4}$ alkylamino group, by reaction with an appropriate alkoxide or amino compound, for example NaOCH$_3$ or HN(CH$_3$) in a suitable solvent, e.g. methanol or dimethylformanide (DMF) preferably in the presence of a base. It will be appreciated that similar displacements may also be performed at various stages of the preparation of compounds of formula (I').

(iii) At an appropriate point in a synthetic route to a compound of formula (I'), protecting one or more functional groups (for example, converting the central carbonyl group to a ketal group) and in a later or final step, deprotecting in order to regenerate the desired group.

(iv) Where, in a compound of formula (I') or a physiologically acceptable salt thereof, n is 0 to 1, increasing the oxidation state of the sulphur atom so as to form repectively, a corresponding compound or salt wherein n is 1 or 2, or 2. Again, it will be appreciated that oxidation of the sulphur atom may be performed at any appropriate stage of the preparation.

(v) Where, in a compound of formula (I') or a physiologically acceptable salt thereof, $R^1$ or $R^2$ represents an unsubstituted tetrazol-5-yl group, alkylating the said group to form a corresponding compound wherein $R^1$ or $R^2$ as appropriate, represents a $C_{1-4}$ alkyltetrazol-5-yl group. Such alkylation may be performed by any of the methods well known to those skilled in the art, for example by reaction with an alkyl-(e.g., methyl-)halide, for example the iodide.

In process (a) above, the tetrazolyl precursor and reaction conditions may for example be as described in the Batchelor and Hodson specifications.

In process (b), the oxidation may be effected by reaction with hydrogen peroxide in acetic acid, with an organic peracid such as meta-chlorobenzoic acid in an inert solvent, eg. chloroform or dichloromethane, or with an inorganic peracid. Alternative oxidising agents for use in this stage of the process include ozone and alkali metal permanganates. Where the reaction is performed in an organic solvent, a crown ether is preferably included to ensure solution of the product. Other suitable inorganic oxidising agents include alkali metal chromates and dichromates in an unreactive solvent such as acetic acid. When it is also desired to perform the sulphur oxidation of option (iv) above and this does not lead simultaneously to the oxidation of the 9—OH or —H,H groups in process (b), then oxidation to 9—C=0 may be effected by admixture with a catalytic amount of strong base such as an alkali metal hydroxide or alkoxide, e.g. the t-butoxide, thereby promoting the air oxidation.

The compounds of formulae (II) and (III) and their salts may be prepared by processes analogous to those described in the Hodson and Batchelor specifications and also in U.S. Pat. Nos. 4,012,499; 4,025,635; 4,103,015; 4,145,350; and 4,177,257.

The following examples illustrate the present invention.

EXAMPLE 1

7-Isopropyl-3-(2-methyl-2H-tetrazol-5-yl)thioxanthen-9-one 10,10-dioxide (Compound A)

To 7.0 g (0.02 mol) of 7-isopropyl-3-(tetrazol-5-yl)thioxanthen-9-one (prepared by the methods of Hodson and Batchelor) was added sodium hydride, 1.0 of a 50% dispersion in mineral oil (0.08 mol), in dry DMF, 50 ml. The mixture was stirred at room temperature for 10 min., then CH$_3$I, 29.6 g, (0.21 mol), was added and the mixture was stirred for an additional 4.5 hr. The mixture was poured into H$_2$O, and the yellow precipitate was collected by filtration then recrystallized from a mixture of ethanol, DMSO and H$_2$O to provide 5.0 g of yellow crystals of 7-Isopropyl-3-(2-methyl-2H-tetrazol-5-yl)thioxanthen-9-one 10,10-dioxide with m.p. 219°–221° C.; TLC on silica gel (hexane:ethylacetate/4:1), R$_f$=0.21.

Analysis: calc. for C$_{18}$H$_{16}$N$_4$O$_3$S; C, 58.68; H, 4.38; N, 15.21. Found: C, 58.71; H, 4.41; N, 15.17.

EXAMPLE 2

3-(2-Methyl-1H-tetrazol-5-yl)thioxanthen-9-one 10,10 dioxide (Compound B)

The title compound was prepared according to the method described in Example 10 of U.S. Pat. No. 3,905,989, mp. 204°–205° C.

EXAMPLE 3

3-(1-Methyl-1H-tetrazol-5-yl)thioxanthen-9-one 10,10-dioxide (Compound C)

The title compound was prepared in a manner analogous to that described in Example 2 above, m.p. 270°–271° C.

EXAMPLE 4

Pharmaceutical Formulation

In the following formulation examples, 'active ingredient' means a compound of formula (I') as hereinbefore defined or a physiologically acceptable salt thereof, or a pro-drug thereof. When referring to salts, weights are expressed in terms of weight of the anion.

A—100 mg Compression Coated Tablet

|  | Ingredients | Amount per Tablet |
|---|---|---|
| Core | Active Ingredient | 100 mg |
|  | Cornstarch | 25 mg |
|  | Magnesium Stearate | 2 mg |
| Coating | Lactose | 320 mg |
|  | Cornstarch | 50 mg |
|  | Gelatin | 6 mg |
|  | Magnesium Stearate | 4 mg |

The active ingredient and starch are granulated with water and dried. Magnesium stearate is added to the dried granules. Lactose and starch are granulated with a 10% w/v aqueous solution of gelatin and dried. Magnesium stearate is added to the dried granules. The granulated core is compressed with the granulated coating in a conventional compression molding machine.

B—200 mg Capsule

| Ingredients | Amount per Capsule |
| --- | --- |
| Active Ingredient | 200 mg |
| Lactose | 200 mg |
| Talc | 40 mg |

The active ingredient, lactose and talc are brought into intimate admixture with one another and 440 mg of the resultant mixture is introduced into a size 0 hard gelatin capsule.

C—100 mg Capsule

| Ingredients | Amount per Capsule |
| --- | --- |
| Active Ingredient | 100 mg |
| Lactose | 100 mg |
| Cornstarch | 100 mg |
| Magnesium Stearate | 10 mg |

The ingredients are mixed together until homogeneous and the resulting mixture filled into each hard gelatin capsule.

D—500 mg Tablet

| Ingredients | Amount per Tablet |
| --- | --- |
| Active Ingredient | 500 mg |
| Cornstarch | 100 mg |
| Microcrystalline Cellulose | 75 mg |
| Magnesium Stearate | 10 mg |
| Granulated polyvinylpyrrolidone 10% w/v in 50% w/v aqueous ethanol | 5 mg |

The active ingredient, cornstarch and microcrystalline cellulose are mixed together, and granulated with the alcoholic polyvinylpyrrolidone. The resulting granules are dried, and compressed to produce tablets.

E—Suppository

| Ingredients | Amount per Suppository |
| --- | --- |
| Active Ingredient | 200 mg |
| Suppository Base | q.s. 2 g |

The active ingredient in fine powder form is dispersed into a little of the molten suppository base at 50° C. The dispersion is incorporated into the bulk of the base at the same temperature, allowed to cool at 42°–45° C., poured into suitable 2 g suppository molds and allowed to set at 15°–20° C. suppository bases are Massa Esterinum C and Witten H suppository compound.

F—Dispersible Tablet

| Ingredients | Amount per Tablet |
| --- | --- |
| Active Ingredient | 200 mg |
| Cornstarch | 40 mg |
| Primojel (Trade name: sodium starch glycollate (125#m powder)) | 50 mg |
| Dicalcium Phosphate Dihydrate | 50 mg |
| Sodium Carboxymethyl Cellulose | 2 mg |
| Sodium Saccharin | 5 mg |
| Microcrystalline Cellulose | 50 mg |
| Magnesium Stearate | 3 mg |

The active ingredient, half of the cornstarch, the Primojel and dicalcium phosphate are mixed together and then granulated with a solution of sodium carboxymethyl cellulose, and sodium saccharin in a suitable volume of 50% ethyl alcohol. The granules were dried, the remaining cornstarch, the microcrystalline cellulose and the magnesium stearate were blended-in and the resulting mixture compressed into tablets.

I claim:

1. A method of preventing reoccurrence or treatment of a mental disorder in a mammal identified as having had or having a mental disorder, comprising administration to said mammal of a mental disorder reversing amount of a compound of formula (I')

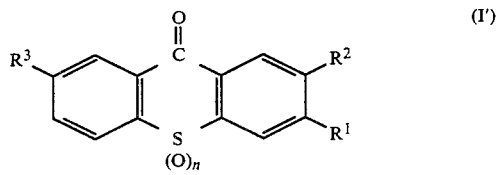

wherein
n is 0, 1 or 2;
one of $R^1$ and $R^2$ is hydrogen and the other is a tetrazol-5-yl group optionally substituted by one or more $C_{1-4}$ alkyl groups; and
$R^3$ is selected from hydrogen, saturated and unsaturated aliphatic hydrocarbon moieties containing from 1 to 4 carbon atoms, groups $OR^4$ (where $R^4$ is selected from hydrogen and saturated and unsaturated aliphatic hydrocarbon moieties containing from 1 to 4 carbon atoms), halo, groups of formula—$NR^5R^6$ (where $R^5$ and $R^6$ are independently selected from hydrogen, $C_{1-4}$ alkyl and hydroxy-$C_{1-4}$ alkyl, provided that the total number of carbon atoms in $R^5$ and $R^6$ does not exceed 4), amino-$C_{1-4}$alkylamino and morpholino);
or a physiologicaly acceptable salt thereof.

2. A method as claimed in claim 1 wherein the mental disorder is selcted from depression, obsessive compulsive states, anxiety states and appetite disorders.

3. A method as claimed in claim 2, wherein the mammal is human.

4. A method as claimed in claim 2, wherein the compound of formula (I) or a physiologically acceptable salt thereof, $R^3$ is selected from hydrogen, saturated and unsaturated aliphatic hydrocarbon moieties containing from 1 to 4 carbon atoms, groups $OR^4$ (where $R^4$ is selected from hydrogen and saturated and unsaturated aliphatic hydrocarbon moieties containing from 1 to 4 carbon atoms), halo, groups of formula —$NR^5R^6$ (where $R^5$ and $R^6$ are independently selected from $C_{1-4}$ alkyl and hydroxy-$C_{1-4}$ alkyl, provided that the total number of carbon atoms in $R^5$ and $R^6$ does not exceed 4), amino-$C_{1-4}$ alkylamino and morpholino.

* * * * *